US011540528B2

(12) United States Patent
Houwelingen-De Jong et al.

(10) Patent No.: US 11,540,528 B2
(45) Date of Patent: Jan. 3, 2023

(54) SALT REDUCTION IN PROCESSED CHEESE COMPOSITIONS, PROCESSED CHEESE COMPOSITION AND USE

(71) Applicant: PURAC BIOCHEM B.V., Gorinchem (NL)

(72) Inventors: Dirkje Houwelingen-De Jong, Gorinchem (NL); Simone Johanna Bouman, Gorinchem (NL)

(73) Assignee: Purac Biochem B.V., Gorinchem (NL)

( * ) Notice: Subject to any disclaimer, the term of this patent is extended or adjusted under 35 U.S.C. 154(b) by 83 days.

(21) Appl. No.: 16/301,121

(22) PCT Filed: May 12, 2017

(86) PCT No.: PCT/EP2017/061478
§ 371 (c)(1),
(2) Date: Nov. 13, 2018

(87) PCT Pub. No.: WO2017/194745
PCT Pub. Date: Nov. 16, 2017

(65) Prior Publication Data
US 2019/0200633 A1    Jul. 4, 2019

(30) Foreign Application Priority Data
May 13, 2016   (EP) .................................. 16169673.7

(51) Int. Cl.
*A23C 19/082* (2006.01)
*A23L 29/00* (2016.01)
*A23L 27/00* (2016.01)
*C12P 7/56* (2006.01)

(52) U.S. Cl.
CPC ............ *A23C 19/082* (2013.01); *A23L 27/88* (2016.08); *A23L 29/035* (2016.08); *C12P 7/56* (2013.01); *A23C 2250/10* (2013.01); *A23V 2002/00* (2013.01); *A23V 2200/16* (2013.01); *A23V 2200/222* (2013.01); *A23V 2250/042* (2013.01); *A23V 2250/1582* (2013.01); *A23V 2250/1614* (2013.01); *A23V 2250/5424* (2013.01)

(58) Field of Classification Search
CPC ... A23C 19/082; A23C 2250/10; A23L 27/88; A23L 29/035; C12P 7/56; A23V 2002/00; A23V 2200/16; A23V 2200/222; A23V 2250/042; A23V 2250/1582; A23V 2250/1614; A23V 2250/5421; A23V 2250/063

USPC ......................................................... 426/582
See application file for complete search history.

(56) References Cited

U.S. PATENT DOCUMENTS

| | | | |
|---|---|---|---|
| 2,317,958 A | 4/1943 | Ingle et al. | |
| 5,935,634 A * | 8/1999 | Gamay ................ | A23C 19/082 426/582 |
| 2009/0047396 A1 * | 2/2009 | Ikeda ...................... | A23L 27/40 426/271 |
| 2013/0071544 A1 * | 3/2013 | Alexander .............. | A23L 19/00 426/615 |
| 2015/0157036 A1 * | 6/2015 | Marcus-Johnson ....... | C12R 1/46 426/9 |
| 2015/0353611 A1 * | 12/2015 | Sliekers ............... | C07K 14/335 424/780 |

OTHER PUBLICATIONS

Da Silva et al., "Equivalence salting and temporal dominance of sensations analysis for different sodium chloride substitutes in cream cheese", International Journal of Dairy Technology, vol. 67, No. 1, Oct. 4, 2013, pp. 31-38.
Cichoski et al., "Effect of the addition of probiotics on the characteristics of reduced-fat "prato" cheese manufactured with fibers and potassium lactate", Food Science and Technology (Campinas), vol. 28, No. 1, Mar. 2008, pp. 214-219. (with English abstract).
International Search Report issued in PCT/EP2017/061478, dated Jul. 4, 2017.
Written Opinion of the International Searching Authority issued in PCT/EP2017/061478, dated Jul. 4, 2017.

* cited by examiner

*Primary Examiner* — Erik Kashnikow
*Assistant Examiner* — Bhaskar Mukhopadhyay
(74) *Attorney, Agent, or Firm* — Foley & Lardner LLP

(57) ABSTRACT

The present invention concerns the field of processed cheese compositions, and, more particularly, relates to reduced salt processed cheese compositions. The present invention derives from the surprising finding that potassium lactate can be used in the manufacture of processed cheese compositions with reduced sodium content, without detrimental consequences on the taste of the final product. A processed cheese composition according to the invention imparts to the final product an improved flavour perception, as well as strengthening salty, savoury and cheesy taste. An additional surprising finding of the method of the invention is that the use of potassium lactate according to the invention has beneficial consequences on the safety and shelf life of the final product. The use of potassium lactate, in particular potassium lactate in the form of a fermentation product in accordance with the invention, also obviates the need to incorporate artificial flavorings and flavor enhancers, which results in a product with an improved label.

Figure 1:
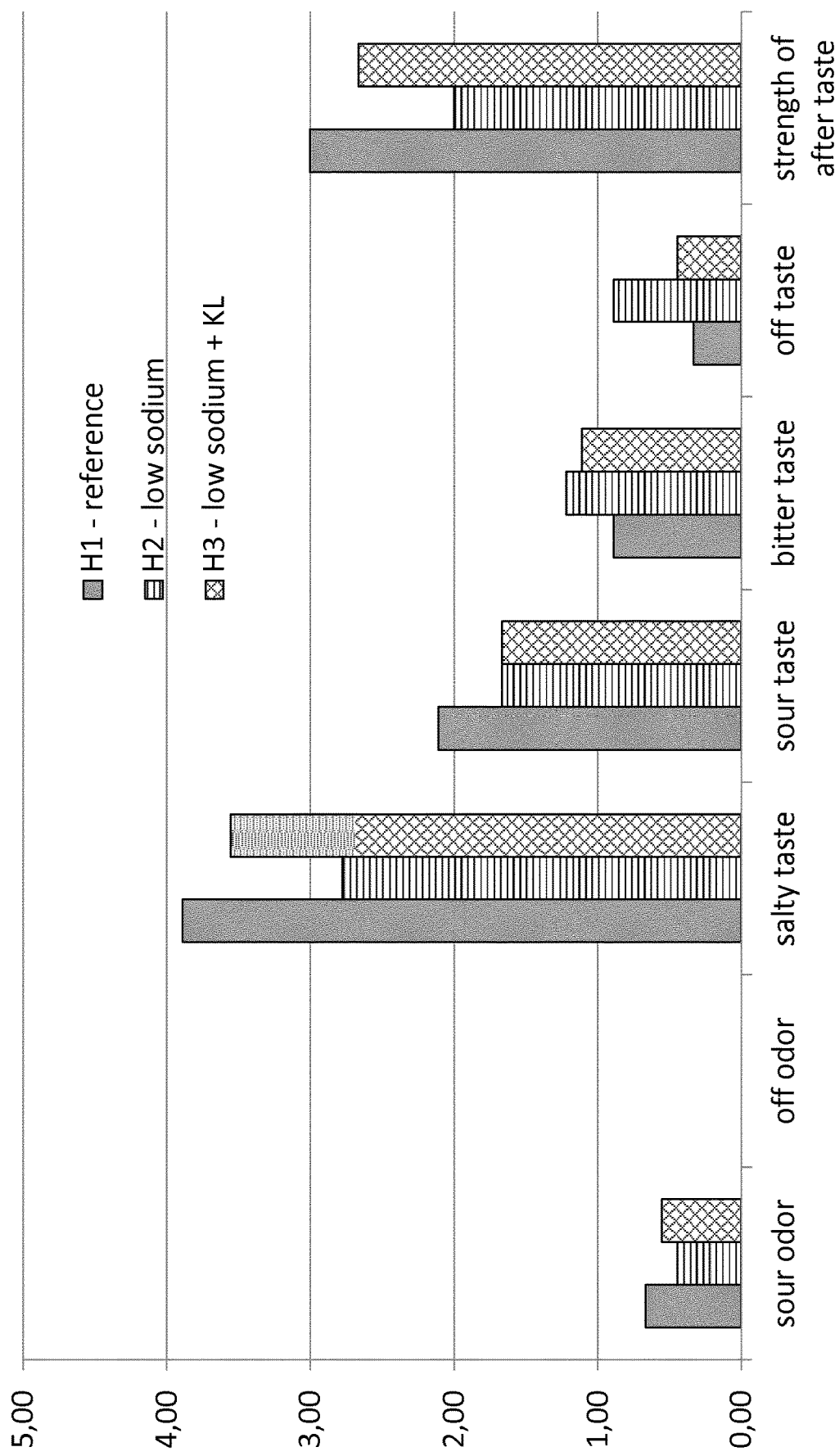

11 Claims, 2 Drawing Sheets

SALT REDUCTION IN PROCESSED CHEESE COMPOSITIONS, PROCESSED CHEESE COMPOSITION AND USE

CROSS-REFERENCE TO RELATED APPLICATIONS

This application is the National Phase of International Patent Application No. PCT/EP2017/061478, filed May 12, 2017, published on Nov. 16, 2017 as WO 2017/194745 A1, which claims priority to European Application No. 16169673.7, filed May 13, 2016. The contents of these applications are herein incorporated by reference in their entirety.

FIELD OF THE INVENTION

The present invention concerns the field of processed cheese compositions, and, more particularly, relates to reduced salt processed cheese compositions.

BACKGROUND OF THE INVENTION

Processed cheese is broadly defined as a blend of one or more natural cheeses of different ages, emulsifying agents, water, and other dairy and nondairy ingredients. The mixture undergoes heating and continuous agitation to produce a pasteurized product that is homogeneous and has an extended shelf life. Processed cheeses are dairy products with relatively high sodium content. This is partly caused by salt present in cheese (accounting for approximately 28% to 37% of the final sodium content), partly by sodium-based emulsifying salts that are used in processing to get the required product characteristics (approximately 44% to 48%), and finally by the further addition of salt (approximately 15% to 28%).

Excessive intake of sodium is known to be a risk factor for many diseases including hypertension, and nowadays a large number of health guidelines recommend to limit the intake of sodium chloride. To decrease the sodium content in processed cheeses the emulsifying salts can be replaced by non-sodium salts (such as potassium-based salts) and added sodium chloride can be reduced or removed.

However, the salt plays an important role in the food safety of cheese because the amount of salt in the moisture phase of the cheese controls the growth of microorganisms. Indeed, to date, the body of evidence for the safety of processed cheese relies heavily on high amounts of sodium chloride in the product. Models developed to ensure the microbiological safety of processed cheese are based on the inhibitory effects of sodium phosphate-based emulsifying salts in combination with pH, water activity, and sodium chloride. As a matter of fact, processed cheese falls into the category of low-acid canned foods due to its chemical composition and pH. Therefore, anaerobic spore-forming organisms such as *Clostridium* spp. are one of the major concerns in processed cheese.

In addition, reducing sodium has a very negative impact on the taste of the product. Despite a number of attempts to compensate salt reduction with flavor enhancers, there is currently no satisfactory solution to manufacture a processed cheese composition with a low sodium content and a taste acceptable for consumers.

It is thus the objective of the present invention to provide a processed cheese composition with reduced levels of sodium, with improved organoleptic properties and/or microbial stability.

Furthermore, there also has been an increased desire to provide foods that contain an increased amount of natural ingredients or ingredients perceived as natural by the consumer.

SUMMARY OF THE INVENTION

The present invention derives from the surprising finding that potassium lactate can be used in the manufacture of processed cheese compositions with reduced sodium content. As will be illustrated in the appending examples, the present inventors have found that the use of potassium lactate allowed for a sodium reduction of up to 50% without detrimental consequences on the taste of the final product. As a matter of fact, a processed cheese composition according to the invention imparts to the final product an improved flavour perception, as well as strengthening salty, savoury and cheesy taste.

An additional surprising finding of the method of the invention is that the use of potassium lactate according to the invention has beneficial consequences on the safety and shelf life of the final product. Although the inventors do not wish to be bound by any particular theory, the use of potassium lactate according to the invention results in a processed cheese composition with a decreased water activity, as illustrated in the examples. Water activity is critical to the shelf life and the microbial stability of the product. Every microorganism is indeed characterized by a water activity level below which it cannot grow. A decrease in water activity for the final product thus directly correlates with fewer microorganisms capable of developing, which impacts safety of the product, and also a slower rate of development of microorganisms, which impacts the shelf life of the product.

The use of potassium lactate according to the invention has another advantage in that it obviates the need to incorporate artificial flavorings and flavor enhancers, which results in a product with an improved label.

Particularly good results have been obtained with potassium lactate containing fermentation products.

These and other aspects of the invention will become apparent for those skilled in the art based on the following detailed description and the appending examples.

DETAILED DESCRIPTION

Hence, in a first aspect, the invention provides processed cheese composition comprising potassium lactate as a salty taste enhancer. More in particular a processed cheese composition is provided, comprising a homogeneous melt or blend of at least natural cheese and/or concentrated milk protein composition; water; one or more emulsifying agents; and potassium lactate in an amount of at least 0.1 wt. %.

As used herein, the term "Processed cheese" generally refers to a specific class of cheese products that are produced by comminuting, mixing and heating a natural cheese or cheese base into a homogeneous, plastic mass, with emulsifying agents and optional ingredients, depending on the class of processed cheese produced. Generally stated, processed cheese has the form of an emulsion/suspension of milk fat droplets in a continuous hydrated protein phase. This is created when natural cheese is subjected to a process of melting and mixing in the presence of processing (emulsifying) salts. The processing salts convert the insoluble protein (calcium paracasein) to soluble sodium caseinate through the process of ion exchange, resulting in a stable, continuous phase. When the hot processed cheese is formed, it is a homogeneous pumpable, fluid cheese material that may be formed into sheets, slices or other desired forms.

The term "natural cheese" generally refers to cheese made from milk by adding a coagulating agent (such as rennet or acid). It may or may not contain starter bacteria, adjunct bacteria or exogenous enzymes. Examples of natural cheeses include, but are not limited to, curd products, Cheddar, Mozzarella, Colby, Monterey Jack, Swiss (Emmental), Gouda, Edam, Feta, Gruyere, Blue, Queso Fresco, Queso Blanco, Ricotta, etc. The natural cheese used in the processed cheese described herein may be freshly made or aged. Preferably the cheese material will have a pH of less than 5.6, a moisture content of less than 60% and contain one or more coagulating agents. Preferably, the cheese material will contain at least 15% protein by weight, more preferably at least 20% protein by weight and preferably at least 10% casein by weight.

The processed cheese may include a range of amounts of the natural cheese component, depending on the form and composition of the natural cheese component and the desired form of the processed cheese. In an embodiment of the invention, a processed cheese composition as defined herein is provided, wherein said homogeneous melt or blend comprises natural cheese solids in an amount within the range of 10-90 wt. %, based on the total solids of the processed cheese composition, preferably within the range of 20-70 wt. %, more preferably within the range of 30-60 wt. %.

Instead of or in addition to the natural cheese, the processed cheese of the present invention may comprise a concentrated milk protein composition. The term "concentrated milk protein composition" means any liquid or dried dairy-based concentrate comprising milk, skim milk, or milk proteins such that the concentrate has a casein to whey ratio between 1:9 and 9:1 by weight and a casein content above 3% (w/v). A milk protein concentrate is a preferred concentrated milk protein composition for use in the invention. The term "milk protein concentrate" (MPC) refers to a milk protein product in which greater than 50%, preferably greater than 70%, most preferably greater than 80% of the non-fat solids is milk protein (on a dry weight basis) and the weight ratio of casein to whey proteins is substantially the same as or higher than that of the milk from which it was prepared.

The processed cheese may include a range of amounts of the concentrated milk protein composition, depending on the form and composition of the natural cheese component and the desired form of the processed cheese. In an embodiment of the invention, a processed cheese composition as defined herein is provided, wherein said homogeneous melt or blend comprises milk protein in an amount within the range of 10-90 wt. %, based on the total solids of the processed cheese composition, preferably within the range of 20-70 wt. %, more preferably within the range of 30-60 wt. %. In another embodiment, the processed cheese may include about 10 to about 90 wt. % of concentrated milk protein composition. According to another embodiment, the processed cheese may include about 30 to about 60 wt. % of concentrated milk protein composition. In yet another embodiment, the processed cheeses herein may include about 35 to about 55 wt. % of concentrated milk protein composition.

The processed cheese may also include a number of other dairy ingredients from various sources as needed for a particular application. For example the processed cheese may include whey protein concentrate; milkfat/cream and the like. As is known by one of ordinary skill in the art, the ingredients may be used in varying amounts in the processed cheese depending on the desired characteristics of the cheese product The processed cheese of the present invention further comprises one or more emulsifying agents, more preferably one or more emulsifying salts. The term "emulsifying agent" as used herein means any food-grade emulsifying agent. Emulsifying agents typically used in the making of processed cheese are those capable of acting as calcium sequestering (or chelating) agent and of solubilizing the proteins. Emulsifying agents also reduce the tendency for tiny fat globules in the cheese to coalesce and pool on the surface of the molten cheese. The person skilled in the art is well aware of many suitable emulsifying agents conventionally used for this purpose. In an embodiment of the invention, the emulsifying agent is an emulsifying salt or a mixture of emulsifying salts, such as one or any mixture of two or more of the following inorganic salts: monosodium phosphate, disodium phosphate, dipotassium phosphate, trisodium phosphate, sodium metaphosphate, sodium acid pyrophosphate, tetrasodium pyrophosphate, tetra potassium pyrophosphate, sodium tripolyphosphate, sodium aluminum phosphate, (tri-) sodium citrate, (tri-)potassium citrate, calcium citrate, sodium tartrate, and sodium potassium tartrate. The choice of the emulsifying agents is dependent on the desired characteristics of the processed cheese product. In a preferred embodiment of the invention, said emulsifying salt does not contain sodium containing emulsifying salts. Preferred are potassium containing salts.

In an embodiment of the invention, a processed cheese composition as defined herein is provided, wherein said homogeneous melt or blend comprises 0.1-5 wt. % of the one or more emulsifying agents, preferably one or more emulsifying salts, based on the total weight of the melt or blend, preferably in an amount within the range of 0.5-4 wt. %, more preferably in an amount within the range of 1-3 wt. %.

The processed cheese composition of the invention will also contain a quantity of water. In the process of making a processed cheese according to the invention, water acts as the medium for dissolving and/or dispersing the various ingredients during melting. The water is important in that, for optimal results, the emulsifying agents need to become fully dissolved and the paracaseinate needs to become fully hydrated. Water may be added to the processed cheese composition by any method. Of course, moisture can also enter into the product through the various ingredients, such as through the natural cheese and/or concentrated milk protein composition. Overall moisture of the final cheese products includes all moisture independent of how the water was introduced into the final product. In an embodiment of the invention, a processed cheese composition as defined herein is provided, wherein said homogeneous melt or blend has a total water content within the range of 45-85 wt. %, based on the total weight of the melt of blend, preferably within the range of 50-80 wt. %, more preferably within the range of 55-75 wt. %.

In an embodiment of the invention, the processed cheese composition is characterized by a total protein content in excess of 4 wt. %, based on the total weight of the composition, preferably in excess of 5 wt. %, more preferably in excess of 6 wt. %, even more preferably in excess of 10 wt. %.

In an embodiment of the invention, the processed cheese composition is characterized by a total content of mono-, di- and trisaccharides below 20 wt. %, based on the total weight of the composition, preferably below 15 wt. %, more preferably below 10 wt. %, most preferably below 7.5 wt. %.

In an embodiment of the invention, the processed cheese composition is characterized by a ratio of total protein content to total content of mono-, di- and trisaccharides (w/w) in excess of ½, preferably in excess of 1, more preferably in excess of 1.5.

In an embodiment of the invention, the processed cheese composition is characterized by a total fat content in excess of 5 wt. %, based on the total weight of the composition, more preferably in excess of 10 wt. %, even more preferably in excess of 12.5 wt. %, most preferably in excess of 15 wt. %.

In accordance with the invention, the processed cheese composition contains a quantity of potassium lactate. In accordance with the invention, potassium lactate is typically added to compensate for the loss in organoleptic properties and/or the loss in microbial stability as a consequence of reductions in sodium content, i.e. compared to prior art processed cheese compositions. The amount of the potassium lactate can vary widely, depending on the amount of sodium containing compounds that is still applied and depending on the specific characteristics of the products desired. In an embodiment of the invention, a processed cheese composition as defined herein is provided, wherein said homogeneous melt or blend comprises potassium lactate in an amount within the range of 0.1-5 wt. %, based on the total weight of the homogeneous melt or blend, preferably in an amount within the range of 0.2-4 wt. %, more preferably in an amount within the range of 0.3-3.5 wt. %, still more preferably within the range 0.4-3 wt. %, most preferably within the range of 0.5-2.5 wt. %.

In an embodiment of the invention, the potassium lactate is incorporated in the form of a fermentation product, such as a partly neutralized or completely neutralized lactic acid ferment. Fermentation products, in accordance with the invention, typically are crude or partially purified/clarified ferments. Such fermentation products have favorable organoleptic profiles, which contribute positively to the taste and flavour characteristics of food products to which they are added. They may also have an extra antimicrobial effect. Moreover, such fermentation products will provide additional benefits with regard to labeling and regulatory aspects.

In one embodiment, the fermentation product is the supernatant obtainable by fermentation of a fermentable substrate with a lactic acid producing microorganism followed by separating supernatant from (wet) biomass and other solid particles.

In one embodiment of the invention, the fermentation product is a concentrated supernatant obtainable by fermentation of a fermentable substrate with a lactic acid producing microorganism followed by separating supernatant from (wet) biomass and other solid particles and concentrating the supernatant.

In an embodiment, the fermentation product comprises a total amount of lactate compounds, including lactic acid and lactic acid salts, in an amount within the range of 10-95 wt. %, based on the total dry weight of the fermentation product, more preferably 45-80 wt. %. In some embodiments the fermentation product contains at least 65 wt. % potassium lactate. In other embodiments, it contains at least 75 wt. % potassium lactate. In yet other embodiments, it contains at least 80 wt. % potassium lactate.

Fermentation products, in accordance with the invention are obtainable by fermentation of a fermentable substrate with a suitable microorganism, in this case a lactic acid producing microorganism, resulting in a composition typically comprising, besides the lactic acid component, traces of the fermentable substrate, metabolites produced by the microorganism, and traces of the microorganism itself, e.g. cellular debris and/or cellular components. As such, a liquid fermentation product is distinguishable from e.g. highly purified products. The term however does not exclude products which have been subjected to some form of purification/clarification and/or concentration.

As will be clear to those skilled in the art, fermentation products can comprise traces of other dispersed or dissolved solids besides the lactate component. Typical examples of such other dispersed or dissolved solids include sugars, such as lactose, glucose and sucrose; other organic acids and/or salts thereof, such as citric acid, pyruvic acid, malic acid, succinic acid, formic acid and acetic acid; nitrogen containing substances, such as amino acids, peptides and proteins; nucleic acid components such as DNA and RNA fragments, nucleotides and nucleosides; cell membrane phospholipids; vitamins; trace elements; and pigments. In an embodiment of the invention, the liquid fermentation product comprises at least one, at least two, at least three, at least four or at least five components selected from the group consisting of lactose, glucose, sucrose, citric acid and salts thereof, pyruvic acid and salts thereof, malic acid and salts thereof, succinic acid and salts thereof, formic acid and salts thereof, acetic acid and salts thereof, propionic acids and salts thereof, amino acids and peptides. In a preferred embodiment of the invention the liquid fermentation product comprises at least 0.5 wt. % on a dry solids weight basis, preferably at least 1 wt. %, more preferably at least 2 wt. % of one or more components selected from the group consisting of lactose, glucose, sucrose, citric acid and salts thereof, pyruvic acid and salts thereof, malic acid and salts thereof, succinic acid and salts thereof, formic acid and salts thereof, acetic acid and salts thereof, propionic acids and salts thereof, amino acids, peptides and proteins.

In an embodiment, the fermentation product comprises formate compounds in an amount within the range of 0.015-2 wt. % based on the total dry weight of the fermentation product.

In an embodiment, the fermentation product comprises acetate compounds in an amount within the range of 0.015-2 wt. %, based on the total dry weight of the fermentation product.

In an embodiment, the fermentation product comprises 2-hydroxybutyrate in an amount within the range of 0.01-1 wt. %, based on the total dry weight of the fermentation product.

In an embodiment, the fermentation product comprises succinate in an amount within the range of 0.01-3 wt. %, based on the total dry weight of the fermentation product.

In an embodiment, the fermentation product comprises residual sugars in an amount of 0.01-20 wt. %, based on the total dry weight of the fermentation product. The residual sugars comprise amongst others glucose (e.g. about 0.01-5 wt. % based on the total dry weight of the fermentation product) and fructose (e.g. about 0.01-5 wt. % based on the total dry weight of the fermentation product). The fermentation product of the present invention may also comprise poly/oligosaccharides of varying length and composition such as for example and not limited to poly/oligosaccharides composed of glucose, galactose, rhamnose, glucosamine, mannose, and xylose. The poly/oligosaccharides content in the lactate salt ferment of the present invention may e.g. be within the range of 0.01-5 wt. %, based on the total dry weight of the fermentation product.

The fermentation product may further comprise some furans such as for example and not limited to 5-hydroxymethyl-2-furfural, furfuraldehyde, 2-furyl methyl ketone and/or 5-methyl furfural and also some aldehydes, such as acetaldehyde, isobutyraldehyde and 5-methyl-2-furancarboxaldehyde. These furans and aldehydes have been found to also have a positive contribution to the flavor and aroma profile of the lactate salt ferment.

The fermentation product, in an embodiment, is further characterized in that it results in a pH within the range of 5-8, when dissolved at 10 wt. % based on dry solids weight in distilled water. In preferred embodiments the fermentation product comprising potassium lactate is a clear liquid solution or concentrate.

In an embodiment of the invention, a processed cheese composition as defined herein is provided, wherein said homogeneous melt or blend comprises a fermentation product as defined here above, in an amount within the range of 0.2-8 wt. %, based on the total weight of the homogeneous melt or blend, preferably in an amount within the range of 0.3-7 wt. %, more preferably in an amount within the range of 0.4-6.5 wt. %, still more preferably within the range 0.5-6 wt. %, most preferably within the range of 0.6-5.5 wt. %.

The processed cheese composition of the present invention can contain other optional ingredients, which may be added to improve texture, flavor, nutrition, and/or cost attributes. These include, but are not limited to, whey derived ingredients (e.g. whey protein concentrate), non-fat dry milk, milk protein concentrate, anhydrous milk fat, gums, starches, gelatin, salt, flavorings, fortifications, colorants, vitamins, etc.

Salt may typically be added as needed. Conventionally, processed cheeses often comprises up to about 5 percent added salt. The present invention, in particular, allows for a reduction in added salt without a substantial deterioration of the perceived organoleptic properties.

Hence, in an embodiment, a processed cheese composition as defined herein is provided, comprising less than 1.0 wt. %, based on the total weight of the composition, of sodium cations, preferably less than 0.8 wt. %, more preferably less than 0.7 wt. %, most preferably less than 0.6 wt. %

In an embodiment, a processed cheese composition as defined herein is provided, comprising less than 2.5 wt. %, based on the total weight of the composition, of sodium chloride, preferably less than 2 wt. %, more preferably less than 1.8 wt. %, most preferably less than 1.6 wt. %

In an embodiment, a processed cheese composition as defined herein is provided, wherein the molar ratio of potassium cations to sodium cations (K+:Na+) exceeds 1/20, preferably it exceeds 1/15, more preferably it exceeds 1/10, more preferably it exceeds 1/8, more preferably it exceeds 1/5, more preferably it exceeds 1/2, most preferably it exceeds 1/1.

In an embodiment of the invention, a processed cheese composition as defined herein is provided, wherein the water activity (Aw) of the processed cheese composition is within the range of 0.8-0.990, preferably within the range of 0.85-0.980, more preferably within the range of 0.9-0.970 In an embodiment of the invention, a processed cheese composition as defined herein is provided, wherein the pH of the processed cheese composition is within the range of 5.0-7.0, preferably within the range of 5.2-6.5, more preferably within the range of 5.3-6.0

A second aspect of the invention, concerns a method of producing a processed cheese composition comprising the steps of:

i) providing a natural cheese composition or a concentrated milk protein composition; water and one or more emulsifying salts;
ii) providing a source of potassium lactate; and
iii) combining the natural cheese composition, water, one or more emulsifying salts and the source of potassium lactate and producing a liquid homogeneous melt or blend there from.

In the method of the invention, the starting materials are typically comminuted in a mixing device and subsequently brought to a liquid state by heating. The temperature in this stage lies between the melting point of the product mixture and 100° C., typically in the range of from about 70° C. to about 90° C. In some embodiments of the invention, the liquid product stream may be heated to ultra-high temperatures in order to kill bacteria, e.g. by shortly heating to temperatures above about 100° C. under elevated pressure. Methodologies of making processed cheeses of the type the present invention is concerned with are within the common general knowledge of those skilled in the art.

In an embodiment of the invention, step ii) of the method comprises the production of a fermentation product in accordance with what has been described herein before.

In general, the production of lactic acid by fermentation of a fermentation broth is well known in the art. The fermentation substrate consists of carbohydrates, originating from corn sugar, cane sugar, beet sugar or mixtures hereof, together with suitable mineral and proteinaceous nutrients.

Lactic acid producing microorganisms that may suitably be used for such fermentation may include bacteria, fungi and yeasts. Lactic acid producing microorganisms may be selected from species that are (a) homolactic lactic acid producers, (b) heterofermentative species which produce lactic acid or (c) species that are genetically modified to produce lactic acid. Examples of such species include but are not limited to species of bacteria such as *Lactobacillus, Leuconostoc, Pediococcus, Lactococcus, Streptococcus, Aerococcus, Carnobacterium, Enterococcus, Oenococcus, Sporolactobacillus, Tetragenococcus, Vagococcus, Weissella, Bacillus* (including *Bacillus coagulans, Bacillus licheniformis, Bacillus smithii, Bacillus thermolactis* and *Bacillus thermoamylovorans*), *Geobacillus* (including *Geobacillus stearothermophilus* and *Geobacillus thermoglucosidans*), *Caldicellulosiruptor* (including *Caldicellulosiruptor saccharolyticus*), *Clostridium* (including *Clostridium thermocellum*), *Thermoanaerobacterium* (including *Thermoanaerobacterium saccharolyticum*), *Thermoanaerobacter* and *Escherichia* (including *Escherichia coli*) and species of fungi and yeast such as *Saccharomyces* (including *Saccharomyes cerevisiae*), *Kluyveromyces* (including *Kluyveromyces lactis* and *Kluyveromyces marxianus*), *Issatchenkia* (including *Issatchenkia orientalis*), *Pichia*(including *Pichia stipitis*), *Candida* (including *Candida boidinii, Candida magnolia, Candida methanosorbosa, Candida sonorensis* and *Candida utilis*) and *Rhizopus* (including *Rhizopus arrhizus, Rhizopus* microspores and *Rhizopus oryzae*).

Bacterial genera that may be of particular interest are *Lactobacillus, Bacillus* (including *Bacillus coagulans, Bacillus licheniformis, Bacillus smithii, Bacillus thermolactis* and *Bacillus thermoamylovorans*), *Geobacillus* (including *Geobacillus stearothermophilus* and *Geobacillus thermoglucosidans*) and *Escherichia* (including *Escherichia coli*). Additionally or alternatively, preferred bacterial species are those that display optimal growth at a pH in the range of about 5 to about 8.

During fermentation, the pH value of the fermentation medium will usually drop. A drop in pH below a critical value, depending on the microorganism used in the process, could damage the microorganism's metabolic process and bring the fermentation process to a stop. Therefore, a neutralizing agent can be added, i.e. a base such as calcium-, sodium-, magnesium- or potassium-hydroxide or ammonia to the fermentation reaction and thus produce a fermentation medium comprising a lactate salt such as calcium lactate or sodium lactate etcetera. Normally both lactic acid and lactate salt are present in the fermentation medium, the ratio of lactic acid to lactate salt depending on the pH of the fermentation product.

Hence, in an embodiment of the invention, a method is provided as described herein before, wherein step ii) comprises:

iia) providing a nutrient medium comprising a solution of a fermentable substrate and a nitrogen source in an aqueous medium;

iib) inoculating said nutrient medium with lactic acid bacteria; and iic) incubating the inoculated nutrient medium under conditions favorable to the growth and/or metabolic activity of said lactic acid bacteria;

wherein the lactic acid is converted to the potassium salt during or after step iic).

After fermentation, the biomass is removed either partly or completely from the liquid fermentation medium. Usually the biomass is separated by means of filtration, centrifuging, flocculation, coagulation, flotation or combinations thereof.

In one particular embodiment of the invention, the fermentation product comprising potassium lactate is produced and purified according to the methods described in published patent application EP 1797773.

Another aspect of the invention concerns the use of potassium lactate, preferably of a fermentation product comprising potassium lactate, as a salty taste imparting and/or enhancing agent in a processed cheese product, preferably a reduced-sodium processed cheese product.

Another aspect of the invention concerns the use of potassium lactate, preferably of a fermentation product comprising potassium lactate, for partly or completely replacing sodium chloride in a processed cheese product.

Another aspect of the invention concerns the use of potassium lactate, preferably of a fermentation product comprising potassium lactate, for improving the microbial stability of a processed cheese product, preferably a reduced-sodium processed cheese product.

Another aspect of the invention concerns the use of potassium lactate, preferably of a fermentation product comprising potassium lactate, for improving the shelf-life of a processed cheese product, preferably a reduced-sodium processed cheese product.

In accordance with the invention, a sodium reduction from a typical concentration of about 1000 mg sodium per 100 grams of processed cheese composition down to a concentration of below 600 mg sodium per 100 grams of processed cheese composition can be achieved. In one embodiments of the invention, for a sodium reduction of from 30 to 50% in the processed cheese composition, potassium lactate is added at an amount of 0.5-1.0%.

Thus, the invention has been described by reference to certain embodiments discussed above. It will be recognized that these embodiments are susceptible to various modifications and alternative forms well known to those of skill in the art.

Many modifications in addition to those described above may be made to the structures and techniques described herein without departing from the spirit and scope of the invention. Accordingly, although specific embodiments have been described, these are examples only and are not limiting upon the scope of the invention.

Furthermore, for a proper understanding of this document and in its claims, it is to be understood that the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

EXAMPLES

Example 1: Preparation of a Processed Cheese Composition According the Invention Milk Coagulation For making the fresh curd, skimmed milk is heated up until 65-70° C. in a large pan, then acidified with 0.3% PURAC FCC 85, a 85% lactic acid product (Corbion Purac, the Netherlands), diluted in potable water in a proportion of 1:10. The acid solution is added slowly while the milk is constantly stirred.

The curd is separated from the whey using a strainer, then washed with water and pressed against the strainer for a couple minutes. The fresh curd is applied as a cheese ingredient in the preparation of processed cheese. The curd is stored under refrigerated conditions for a period of up to 3-4 days maximally.

Spreadable Processed Cheese Manufacturing

A high fat variant spreadable processed cheese with 20 g fat per 100 g product and a low fat variant with 5 g fat per 100 g product have been prepared. Both the high fat variant and the low fat variant have been prepared with a regular sodium content (1.1% sodium) and with a low sodium content (0.6% sodium). The low sodium content was achieved by adapting the type of emulsifying salt from JOHA S9D to JOHA S9K (both applied in a concentration of 3%, ICL Food Specialties, Ladenburg Germany) and by adapting the amount of salt added. The spreadable processed cheese was prepared as follows.

Dissolve salt, emulsifying salt and Purasal HiPure P Plus, a potassium lactate product with 78% potassium lactate (KL)(Corbion Purac, the Netherlands) in water. Blend together with the fresh curd and cream for 45 seconds or until homogenized.

Transfer the mass to a cooker and heat up until boiling, stirring well so it doesn't burn or stick to pan. Keep the cheese mass cooking for 1-3 minutes. After cooking, the product should look like a homogeneous and smooth dough, without any curds, rather liquid than creamy (while it's still hot). Transfer to glass/plastic recipient for storage under refrigeration.

Example 2: Evaluation of the Taste Characteristics and Water Activity for Different Preparations of Processed Cheese Compositions According the Invention Materials The following spreadable processed cheeses are used in this example:

|  | Sample Code | |
| --- | --- | --- |
| Type of Sample | High Fat | Low Fat |
| reference with regular sodium content | H1 | L1 |
| low sodium content | H2 | L2 |
| low sodium content + 0.85% potassium lactate product (78%) | H3 | L3 |

Analyses

The following parameters are analyzed: taste, pH, water activity, sodium content.

Taste: Two descriptive taste tests are performed with 9 trained panelists. The samples are scored on the attributes sour odor, off odor, salty taste, sour taste, bitter taste, off taste and strength of the after taste on a 6-point scale (0=not perceived; 5=strongly present).

pH: a pH probe is placed in the center of each sample to measure pH. Measurements were carried out in duplo.

Water activity: a quantity of each batch is placed in a cup and water activity is measured. Before measurements each batch is placed at room temperature for 1-2 hours.

Sodium content: the sodium content of the samples is determined by atomic absorption spectrometry, using a Varian spectra 220FS instrument.

Results

Figure 2:
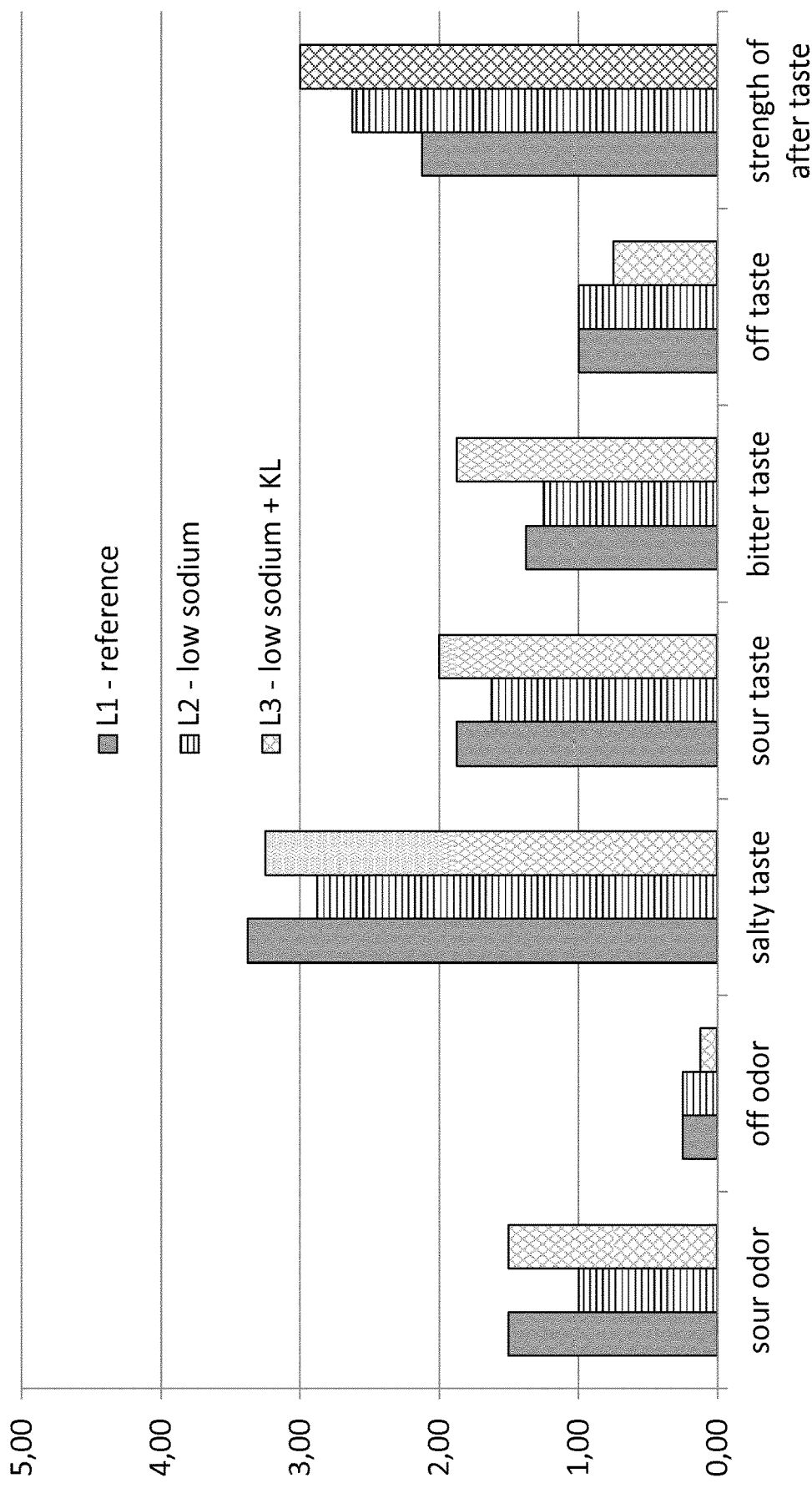

FIGS. 1 and 2 show the results of the taste tests. FIG. 1 shows the results of the test with full-fat spreadable cheese and FIG. 2 shows the results of low fat spreadable cheese.

In FIG. 1 it can be seen that there are no differences in odor between the samples. The low sodium sample H2 has a significantly less salty taste as compared to the reference H1 and has a less strong aftertaste as well. The addition of potassium lactate in H3 however restores the salty taste and the aftertaste to close to that of the reference composition.

In general, the low fat variants have a stronger odor than the high fat variants (FIG. 2). Reducing the salt content (L2) lead to both a less salty and a less sour taste. Although the addition of potassium lactate in L3 lead to a slightly more bitter taste, the salty and sour taste were largely restored to that of the reference product.

The following table shows the results with respect to composition.

|  | moisture [%] | sodium [mg/100 g] | $a_w$ | pH |
| --- | --- | --- | --- | --- |
| H1 | 59 | 1034 | 0.965 | 5.68 |
| H2 | 59.1 | 627 | 0.965 | 5.75 |
| H3 | 59.4 | 567 | 0.964 | 5.76 |
| L1 | 70.7 | 1007 | 0.971 | 5.67 |
| L2 | 70.8 | 589 | 0.970 | 5.76 |
| L3 | 69.9 | 578 | 0.966 | 5.82 |

Lowering the sodium content in spreadable cheese as such was found to not have an effect on the water activity of these products, addition of potassium lactate however lowered the water activity of the products which can have a positive effect on the shelf life of the products.

Summarizing, addition of potassium lactate to spreadable processed cheese with a reduced sodium content can lead to not only an improved taste but also to an improved shelf life due to the lower water activity.

The invention claimed is:

1. A processed cheese composition, comprising a homogeneous melt or blend of:
   (a) natural cheese solids and/or milk protein;
   (b) one or more emulsifying salts in an amount of 1-5 wt %, based on the total weight of the melt or blend, wherein the one or more emulsifying salts are selected from the group consisting of dipotassium phosphate, tetra potassium pyrophosphate, (tri-)potassium citrate, and sodium potassium tartrate;
   (c) potassium lactate in an amount of 0.4 to 3 wt. %, based on the total weight of the melt or blend; and
   (d) water,
   wherein the processed cheese composition comprises less than 0.7 wt. % of sodium cations, wherein the potassium lactate imparts or enhances a salty taste, and wherein the salty taste of the processed cheese composition is substantially the same as the salty taste of a processed cheese composition containing about 1007 mg Sodium cations/100 g processed cheese composition.

2. The processed cheese composition according to claim 1, wherein the amount of potassium lactate in the homogeneous melt or blend is between 0.5 to 2.5 wt. %, based on the total weight thereof.

3. The processed cheese composition according to claim 1, wherein the potassium lactate is incorporated in the form of a fermentation product.

4. The processed cheese composition according to claim 1, wherein the one or more emulsifying salts do not comprise sodium salts.

5. The processed cheese composition according to claim 1, comprising less than 2.5 wt. % of sodium chloride.

6. The processed cheese composition according to claim 1, wherein the stoichiometric ratio of potassium cations to sodium cations (K+:Na+) exceeds 1/8.

7. A method of enhancing or imparting a salty taste to cheese, comprising applying potassium lactate with a processed cheese product in an amount of 0,4-3 wt. %, based on the total weight of the processed cheese composition, wherein the processed cheese product comprises less than 0.7 wt. % of sodium cations, and wherein the salty taste of the processed cheese composition is substantially the same as the salty taste of a processed cheese composition containing about 1007 mg Sodium cations/100 g processed cheese composition.

8. The method according to claim 7, wherein the potassium lactate is in the form of a ferment.

9. The method according to claim 7, wherein the molar ratio of potassium cations to sodium cations (K+:Na+) exceeds 1/20.

10. A method of producing a processed cheese, comprising combining:
    (a) a natural cheese composition or a concentrated milk protein composition;
    (b) one or more emulsifying salts in an amount of 1-5 wt %, based on the total weight of the melt or blend, wherein the one or more emulsifying salts are selected from the group consisting of dipotassium phosphate, tetra potassium pyrophosphate, (tri-)potassium citrate, and sodium potassium tartrate;

(c) a source of potassium lactate comprising potassium lactate in an amount of 0.4 to 3 wt. %, based on the total weight of the combined ingredients; and (d) water, to produce a liquid homogeneous mass therefrom, which comprises less than 0.7 wt. % of sodium cations, and wherein the salty taste of the processed cheese composition is substantially the same as the salty taste of a processed cheese composition containing about 1007 mg Sodium cations/100 g processed cheese composition.

11. The method according to claim 10, wherein the potassium lactate is obtained by:

(a) providing a nutrient medium comprising a solution of a fermentable substrate and a nitrogen source in an aqueous medium;

(b) inoculating the nutrient medium with lactic acid bacteria; and (c) incubating the inoculated nutrient medium under conditions favorable to the growth and/or metabolic activity of the lactic acid bacteria, wherein the lactic acid is converted to the potassium salt during or after step (c).

* * * * *